(12) United States Patent
Sander

(10) Patent No.: US 7,142,359 B2
(45) Date of Patent: Nov. 28, 2006

(54) LIGHTING DEVICE FOR A MICROSCOPE

(75) Inventor: Ulrich Sander, Rebstein (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 0 days.

(21) Appl. No.: 10/793,548

(22) Filed: Mar. 4, 2004

(65) Prior Publication Data

US 2004/0174591 A1 Sep. 9, 2004

(30) Foreign Application Priority Data

Mar. 6, 2003 (DE) .............................. 103 11 000

(51) Int. Cl.
*G02B 21/06* (2006.01)
*G02B 21/00* (2006.01)

(52) U.S. Cl. ...................... 359/385; 359/368; 359/388

(58) Field of Classification Search ........ 359/368–390, 359/618, 633–640; 351/200–247
See application file for complete search history.

(56) References Cited

U.S. PATENT DOCUMENTS

| | | | | |
|---|---|---|---|---|
| 5,126,877 A | | 6/1992 | Biber | ........................ 359/385 |
| 5,446,582 A | | 8/1995 | Takagi et al. | ................ 359/385 |
| 5,627,613 A | * | 5/1997 | Kaneko | ........................ 351/221 |
| 5,703,714 A | * | 12/1997 | Kojima | ........................ 359/368 |
| 5,760,952 A | | 6/1998 | Koetke | ........................ 359/389 |
| 5,856,883 A | | 1/1999 | Sander | ........................ 359/389 |
| 5,898,518 A | * | 4/1999 | Biber | .......................... 359/385 |
| 6,483,642 B1 | | 11/2002 | Deverin | ....................... 359/389 |
| 6,624,932 B1 | | 9/2003 | Koetke | ........................ 359/385 |
| 2001/0040726 A1 | | 11/2001 | Sander | ........................ 359/387 |
| 2003/0048528 A1 | | 3/2003 | Deverin et al. | ............. 359/376 |

FOREIGN PATENT DOCUMENTS

| | | | | |
|---|---|---|---|---|
| DE | 3327672 A1 | | 2/1985 | |
| DE | 19611044 A1 | | 9/1996 | |
| DE | 196 50 773 A1 | | 7/1997 | |
| EP | 1 391 177 A1 | * | 2/2004 | ................ 359/385 |
| GB | 1277979 | | 6/1972 | |
| JP | 9-105866 | * | 4/1997 | ................ 359/385 |

OTHER PUBLICATIONS

English abstract of the Japanese reference No. 10-133122, published on May 22, 1998.*

* cited by examiner

*Primary Examiner*—Thong Nguyen
(74) *Attorney, Agent, or Firm*—Hodgson Russ LLP

(57) ABSTRACT

Lighting device for a microscope comprising at least one observation beam path, in particular a surgical microscope, with an illumination system (3, 4, 5, 28, 29) and a deflection device (8; 48, 49) for deflecting light emitted from the illumination system onto an object to be observed, in particular an eye to be operated on, the deflection device providing an illumination of the object under various illumination angles with regard to the at least one observation beam path, wherein the deflection device comprises two deflection elements (16, 17) at least partly provided as physical beam splitters.

9 Claims, 6 Drawing Sheets

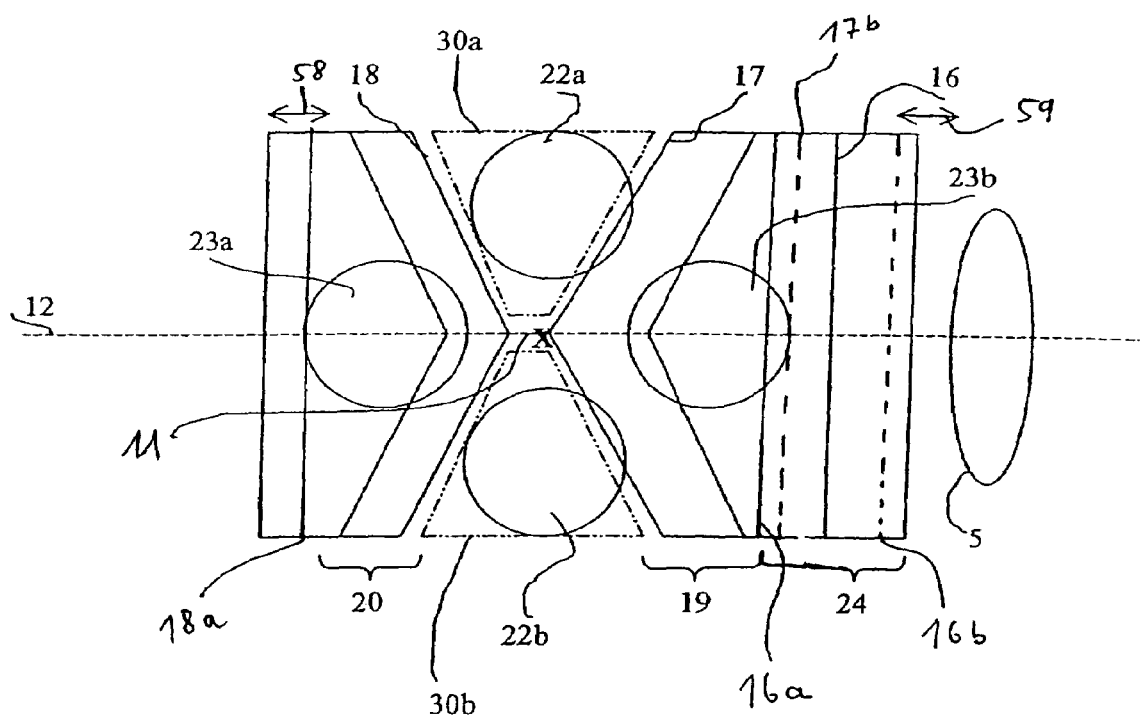
Figur 5

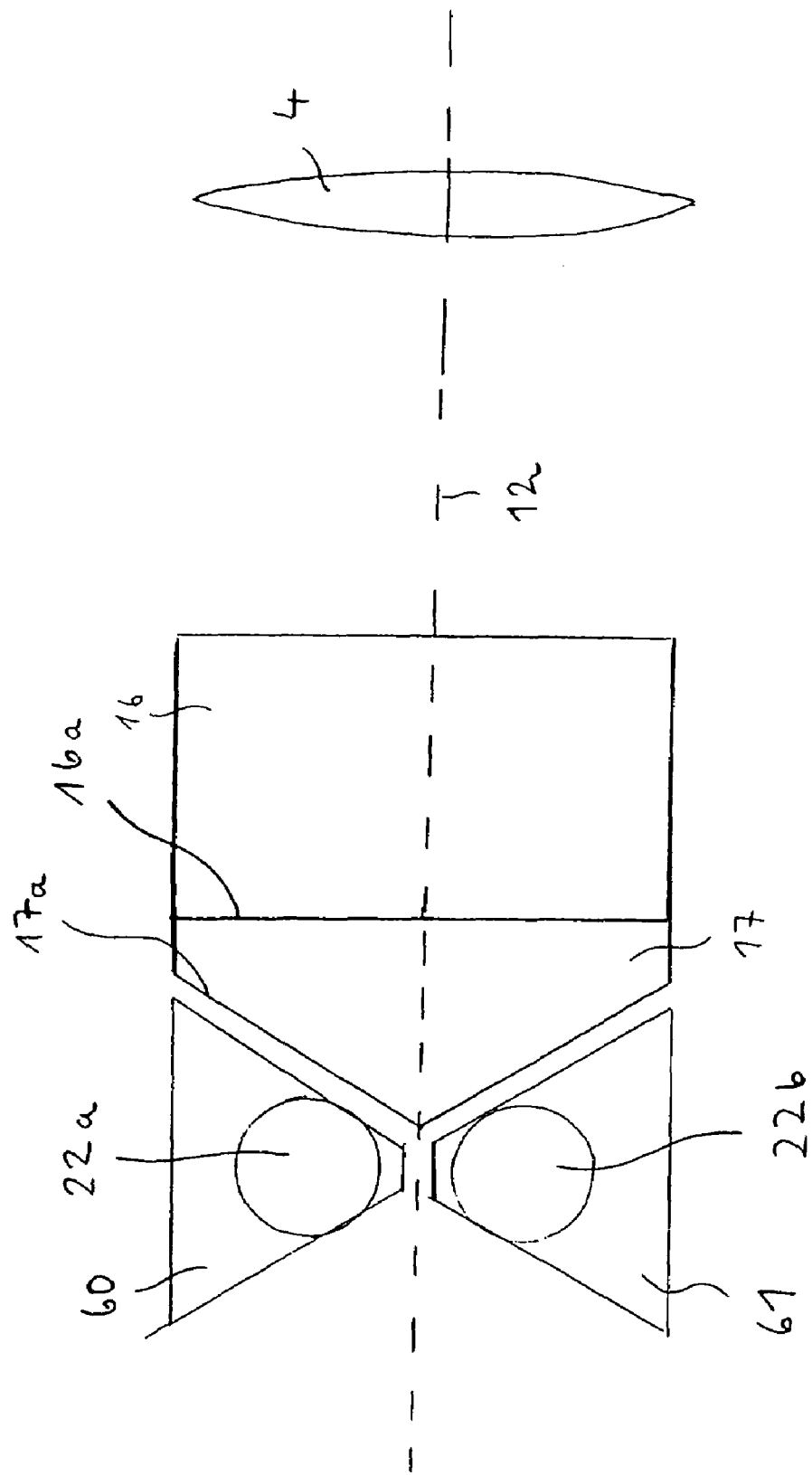

LIGHTING DEVICE FOR A MICROSCOPE

CROSS REFERENCE TO RELATED APPLICATIONS

This application claims priority of the German patent application 103 11 000.3 filed Mar. 6, 2003 which is incorporated by reference herein.

BACKGROUND OF THE INVENTION

This invention concerns a lighting or illumination device for a microscope, in particular a surgical microscope, of a type having at least one observation beam path, an illumination system, and a deflection device for deflecting light emitted from the illumination system onto an object to be observed, for example an eye to be operated on, the deflection device providing an illumination of the object under various illumination angles with regard to the at least one observation beam path.

Lighting devices for surgical microscopes generally use an illumination beam path featuring an angle of approximately 6° (so-called 6° illumination) with respect to the observation beam path. This avoids unwanted shadow formation which would arise in the case of greater angles between the observation beam path and the illumination beam path.

Eye surgery presents further specific requirements with respect to the illumination of a microscope. First of all, sufficient plasticity of the image is achieved with an illumination angle of again approximately 6°. However, for certain surgical ophthalmological observations or operations, it is necessary to produce the so-called red reflex. This involves the pupil of the operated eye being lit up red by light reflected from the retina. This type of illumination is of great significance for example in the case of cataract operations as residual tissue is particularly easy to detect in the back light of the red reflex. The generation of the red reflex requires smaller angles between the observation beam path and the illumination beam path; angles between 0° and 2° are preferable (so-called 2° illumination) here.

Surgical microscopes designed with two pairs of stereoscopic observation beam paths for one main surgeon and one co-observer often have a shortcoming in that, while the main surgeon is able to see the red reflex clearly, the co-observer's view of it is inadequate. Dependent upon his position, either to the right or left of the main surgeon, the co-observer only receives a good red reflex in one of his two observation channels. This interferes with the stereoscopic observation.

A lighting device for a surgical microscope with an illumination system positioned outside the optical axis of the microscopic lens and which illuminates the operation area parallel to the lens axis through the microscope objective, and with a deflection element on the side of the microscope objective facing away from the object, which illuminates the operation area with a fraction of the illuminative light along the objective axis is known from DE 040 28 605. This lighting device is characterised by the illumination system being fitted with a reflection element on the objective side reflecting the illuminating light parallel to the objective axis towards the objective of the microscope, and the deflection element illuminating the area of operation under an inclination angle with respect to the objective axis, this being smaller than the inclination angle under which the reflection element illuminates the area of operation. The greater inclination angle is preferably 6° in this instance, while the smaller one may vary between 0° and 6°.

The disadvantage of this design is that the rays reflected by the deflection element are boundary rays from the lighting aperture of the lighting system, so that an illumination close to the axis, for example under an angle of 2° to the observation beam path, leads to a relatively non-homogeneous and vignetted illumination of the luminous field.

Other lighting devices for surgical microscopes are known from DE 196 50 773 A1 and EP 1 109 046 A1. These lighting devices also use the boundary rays of the lighting device's lighting aperture for illumination close to the axis, leading to the disadvantages specified arising here as well.

Another disadvantage with the state-of-the-art technology is that the surgical microscopes described are designed to be relatively tall, as the 2° and the 6° illumination are arranged on top of each other.

SUMMARY OF THE INVENTION

This invention aims to make available a lighting device for a microscope which enables a more homogeneous illumination of the light field which is freer of vignetting than conventional devices of this kind. The aim is also to provide a compact lighting device in order that the constructional height of a microscope is not increased in an unwanted way.

This aim is achieved through a lighting device comprising an illumination system for emitting light, and a deflection device for deflecting the light emitted by the illumination system onto the object, wherein the deflection device includes two deflection elements each being at least in part a physical beam splitter. This aim is further achieved through a microscope incorporating such a lighting device.

According to this invention, a particularly homogeneous illumination of the luminous field of the microscope is guaranteed, free of vignetting, as, by using deflection elements (to deflect light from one illumination system onto an object to be observed) which are designed as physical beam splitters, essentially the full cross-section of the lighting aperture impacts all mirror or reflecting elements. This use of "physical" beam splitters in the present invention is distinguished from the use of "geometric" beam splitters in prior art lighting devices, wherein only small, fully reflective segments of the deflective elements have been used for deflecting the boundary areas of the lighting aperture (pupil). It is especially possible to position the individual deflection elements along one single optical axis with this deflection device according to the invention, allowing the constructional height of the microscope to be reduced advantageously.

The specification describes advantageous embodiments of the lighting device and the microscope according to the invention.

In accordance with a preferred embodiment of the lighting device according to the invention, the deflection device comprises at least three deflection elements. The particularly preferred embodiment enables for example a 6° illumination, a +2° illumination and a −2° illumination with surgical microscopes.

In accordance with a particularly preferred embodiment of the invention, for which special protection is sought, two deflection elements are arranged in such a way as to enable a +2° and a −2° illumination simultaneously.

This possibility for illumination proves to be particularly advantageous in the case of surgical techniques using a red reflex where the eye can rollingly move. Phacoemulsification is given as an example here. Simultaneous +2° and −2° illumination ensures that the surgeon will not need to make any adjustments to the microscope while working. +2°, −2° and 6° illumination is also possible simultaneously, as is any other combination, which can be set by using appropriately positionable shutters, for example.

Conveniently, at least one of the deflection elements is at least in part fully mirror-coated. This measure allows light cast onto the fully mirror-coated areas to be directed fully on to the object to be observed, thus making it possible to influence the strength of the lighting to one's advantage. Furthermore, in this way, overlaps between the observation beam paths of the microscope and the fully mirror-coated areas can be produced easily. This kind of overlapping is necessary for certain applications within the framework of ophthalmological surgery, for example in the provision or adjustment of the red reflex.

In accordance with a particularly preferred embodiment of the illumination according to the invention, the deflection device is designed as a prism combination comprising part-reflective surfaces. In practice, prism systems have proved to be adjustable relatively easily. However, it is also conceivable to design the deflection device with appropriately positioned part-reflective reflectors (mirrors).

In accordance with a particularly preferred embodiment of the lighting device according to the invention, the deflection device is designed as a single unit or one-piece prism block. With a single unit prism block of this type, it is possible to keep the adjustment required when setting up the microscope to a minimum. Furthermore, this type of prism block proves to be extremely robust during the handling of microscopes.

It is likewise possible and advantageous for the deflection device to feature two prism blocks, spatially separated from one another. This measure for example makes it possible to prevent adhesive joints between the respective prisms of the deflection device disrupting the observation beam paths, which can lead to double images or reflections. It should be noted that the deflection elements could also be designed as reflective or transmissive reflectors, positioned independently of prism blocks.

In accordance with a preferred embodiment of the microscope according to the invention, this microscope is designed as a stereomicroscope. It is particularly preferable here for the stereomicroscope to feature two observation beam paths for a main surgeon and two further observation beam paths for an assistant. In comparison with conventional microscopes of this type, this kind of stereomicroscope comprising observation beam paths for a main surgeon and an assistant allows red reflex characteristics to be adjusted both for the main surgeon and the assistant as required. Using the entire lighting aperture (pupil) generally results in it being possible to prevent vignetting as well as to create a homogenous luminous field for both the main surgeon and the assistant.

The microscope according to the invention advantageously comprises shutters or screens which can be used to turn the illumination beam paths on or off as desired. This makes it possible for example to cut off 0° illumination, thereby making it possible if necessary to avoid the generation of the red reflex.

In accordance with a particularly preferred embodiment of the microscope according to the invention, the deflection device is able to move transversely with respect to the optical axis of the main objective of the microscope. Particular provision is made here for transverse mobility perpendicular to the optical axis of the main objective. This leads to further possibilities for variation in the adjustment of illumination angles and/or overlaps between fully mirror-coated areas of the deflection elements and observation beam paths, through which the formation of the red reflex can be influenced.

In accordance with another preferred embodiment of the microscope according to the invention, for which special protection is sought, the microscope features a deflection device with a deflection element constructed as a physical beam splitter and a further reflective deflection element, glass blocks also being provided, which are positioned in such a way as to allow the observation beam paths of the microscope to run through them. This measure enables the apertures of the observation beam paths to be contracted in an effective manner, thereby making it possible to reduce the constructional height of the microscope. By designing the deflection device appropriately, it is also possible to shorten the length of the deflection device in the direction of the optical axis.

BRIEF DESCRIPTION OF THE DRAWINGS

The invention will now be described further with reference to the accompanying drawings, in which:

FIG. 5 shows a preferred embodiment of the deflection device used according to the invention in the microscope shown in FIG. 4, viewed in the direction of arrow P in FIG. 4; and FIG. 6 shows another preferred embodiment of the deflection device used according to the invention, in the direction of the arrows P in FIGS. 1 and 4.

DETAILED DESCRIPTION OF THE INVENTION

Figure 1:
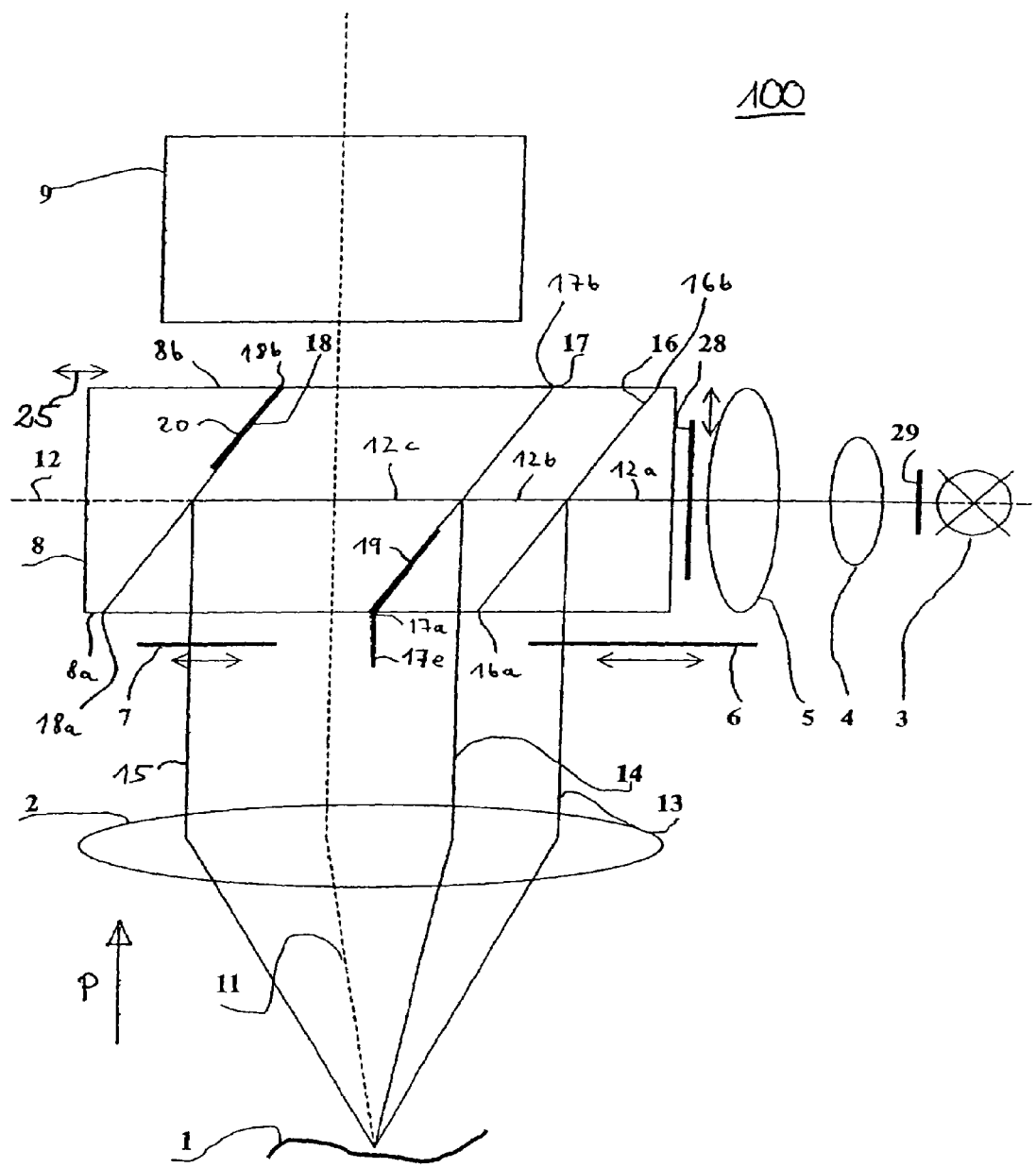
FIG. 1 shows a schematically simplified lateral sectional view of a preferred embodiment of the microscope according to the invention comprising a preferred embodiment of the lighting device according to the invention.

In FIG. 1 a preferred embodiment of the microscope according to the invention is generally designated 100.

The microscope 100 features a main objective (lens) 2 and a magnifying system 9 designed especially as a zoom system. The axis of the entire optical system comprising the main objective 2 and the magnifying system 9 is indicated by numeral 11. The observation channels of the microscope 100 run parallel to this axis 11. As is apparent from FIG. 1, this axis 11 features a sharp bend in the main objective 2, caused by the asymmetrical positioning of the magnifying system 9 in relation to the main objective 2. This asymmetrical positioning of the main objective 2 and the magnifying system 9 proves to be advantageous for certain applications. In the case of a sufficiently large lighting aperture of the 6° illumination (partial beam 13) described further below, with a central or symmetrical alignment of the main objective 2 in relation to the magnifying system 9, the boundary rays would be cut off as, in this case, the right side of the main objective in FIG. 1 would fall into the lighting aperture (pupil) of the partial beam 13.

Light for the illumination of an object 1 to be observed is acquired from a light source 3 via a deflection device formed as a prism block 8 onto the object 1. Two lenses 4, 5 and two screens (shutters) 28, 29 are, for example, provided between the light source 3 and the deflection device 8. All common light sources, in particular coherent and/or incoherent light sources, such as bulbs, fibre lighting, discharge lamps, lasers etc., may be used.

The prism block 8 features 3 deflection elements 16, 17, 18 formed as mirror-coated surfaces.

Deflection element 16 is formed entirely and deflection element 17 is formed at least partly as a physical beam splitter. That is, the beam (cluster) profile of the (schematically shown) light beam 12a from the light source 3 impacting the deflection elements 16, 17 from the right in FIG. 1 remains unchanged. The light beam 12a is distributed evenly over the entire cross-section of the deflection elements 16, 17. It is apparent that the light beam 12a incident along the illumination axis 12 of the deflection device 8 is split by the deflection element 16 into a first partial beam 13, which is reflected, and a second partial beam 12b, which is transmitted. The partial beam 13 provides a 6° illumination for the object 1 after passing through the main objective 2.

The partial beam 12b transmitted by the deflection element 16 is also again partly deflected and transmitted by the second deflection element 17. The reflected partial beam is designated 14 and the transmitted partial beam is designated 12c. The reflected partial beam 14 initially runs substantially parallel to partial beam 13. Partial beam 14 provides a +2° illumination of the object 1 after passing through the main objective 2.

The partial beam 12c transmitted by the deflection element 17 then impacts the third deflection element 18, which is suitably fully mirror-coated. The partial beam designated 15, which is reflected by the deflection element 18, likewise impinges the object 1 after passing through the main objective 2. The partial beam 15 provides a −2° illumination of the object 1. It is possible to cut off or partly screen off partial beams 13, 14, 15 using the shutters 6, 7 provided. During an eye examination, for example, this can avoid disruptive cornea reflexes or improve the contrast of the red reflex.

Figure 2:
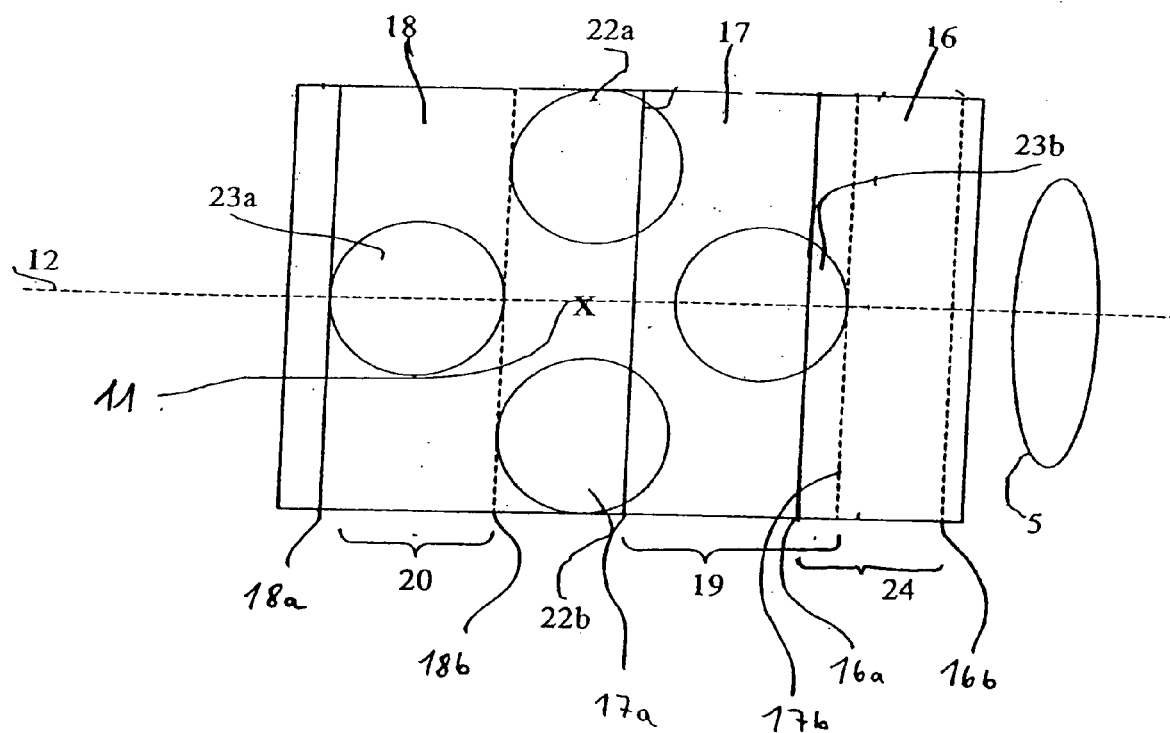
FIG. 2 is a schematic view of a first preferred embodiment of the deflection device used according to the invention, in the direction of arrow P in FIG. 1.

The arrangement of the microscope's observation beam paths in relation to the deflection elements or reflective surfaces 16, 17, 18 already mentioned is presented clearly in FIG. 2. FIG. 2 presents a projection of the deflection elements onto the underside 8a of the deflection device 8. The respective lower edges 16a, 17a, 18a of the deflection elements 16, 17, 18, which actually run along this underside 8a, are presented as continuous lines. The upper edges 16b, 17b, 18b of the deflection elements 16, 17, 18 which run along the top side 8b are presented as dotted lines.

FIG. 2 shows the observation beam paths of the microscope, with two observation beam paths 22a, 22b being provided for the main observer or surgeon and two observation beam paths 23a, 23b being provided for a co-observer or assistant.

It is apparent that the co-observer's beam paths 23a, 23b are fully superimposed by the projection of the deflection elements or reflective surfaces 16, 17, 18 while the main observer's beam paths 22a, 22b are only partly superimposed. The fully or partly mirror-coated areas of the deflection elements 16, 17, 18, are highlighted in FIG. 2 by curly brackets and are designated 24, 19 and 20. It should be pointed out again that, in the embodiment shown in FIG. 2, the mirror-coated areas basically cover the entire surface of the deflection elements 16, 17, 18. For example in the case of fully mirror-coated deflection elements 17, 18, the observation beam paths 23a, 23b are therefore blocked, resulting in this design of microscope only being suitable for stereoscopic observation by one main observer (use of observation channels 22a, 22b).

However, in the case of partly mirror-coated deflection elements 17, 18, observation of the object 1 is possible through the observation channels 23a, 23b as well.

For optimisation of luminous efficiency in the observation beam paths presented, it is preferable for the deflection elements 17, 18 to be, in part, fully mirror-coated (fully reflective), while the non-mirror-coated areas of the deflection elements 17, 18 may be made semi-transparent or partly mirror-coated or transparent. This aspect is now explored in more detail with reference to FIG. 3.

Figure 3:
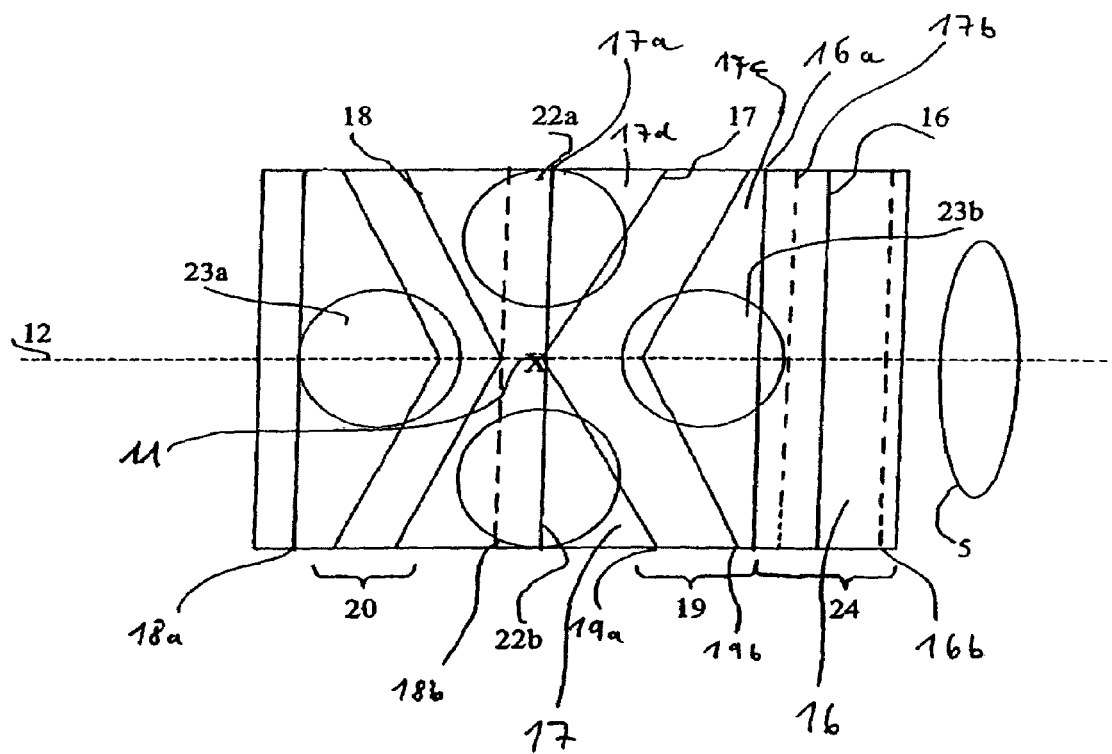
FIG. 3 shows a view of another preferred embodiment of the deflection device used according to the invention, in the direction of arrow P.

The deflection elements 17, 18, as presented in FIG. 3, are characterised by being fully mirror-coated only in part. The lower edges and upper edges of the deflection elements (17, 18) are once again designated 17a/17b and 18a/18b. In the projection presented, an arrow-shaped area 19 is visible between edges 17a/17b of the deflection element 17, said area 19 featuring a lower edge 19a and an upper edge 19b. This area 19 provides the fully mirror-coated area of deflection element 17. The area to the right of the upper edge 19b, identified here as 17c, and the area to the left next to the lower edge 19a, identified as 17d, is transparent in construction in order to reduce the respective overlapping areas between the observation channels 23b or 22a, 22b and the fully mirror-coated area 19. This guarantees largely unimpeded observation through the observation channels 22a, 22b and 23b.

Deflection element 18 is designed analogously and the fully mirror-coated area is once again designated 20. In comparison with the embodiment according to FIG. 2, it is apparent that the overlap area between the fully mirror-coated area 20 and the observation channel 23a is reduced significantly, resulting in the provision of a stereoscopic observation for a co-observer using beam paths 23a, 23b. The overlap areas between the fully mirror-coated area 19 and the observation beam paths 22a, 22b are also reduced in comparison with the embodiment presented in FIG. 2.

The fully mirror-coated areas 19, 20 in FIG. 3 are drawn in schematically in FIG. 1 as bold lines on the deflection elements 17, 18.

It should be noted that a certain amount of overlap of the mirror-coated areas 19, 20 with the observation beam paths 22a, 22b, 23a, 23b is necessary in order to produce the red reflex required for specific applications.

It is possible to optimise this red reflex, for example with respect to intensity and contrast, by suitable dimensioning or design of the fully mirror-coated areas 19, 20 on the deflection elements 17, 18.

Another preferred embodiment of the lighting device according to the invention will now be described with reference to FIGS. 4 and 5.

Figure 4:
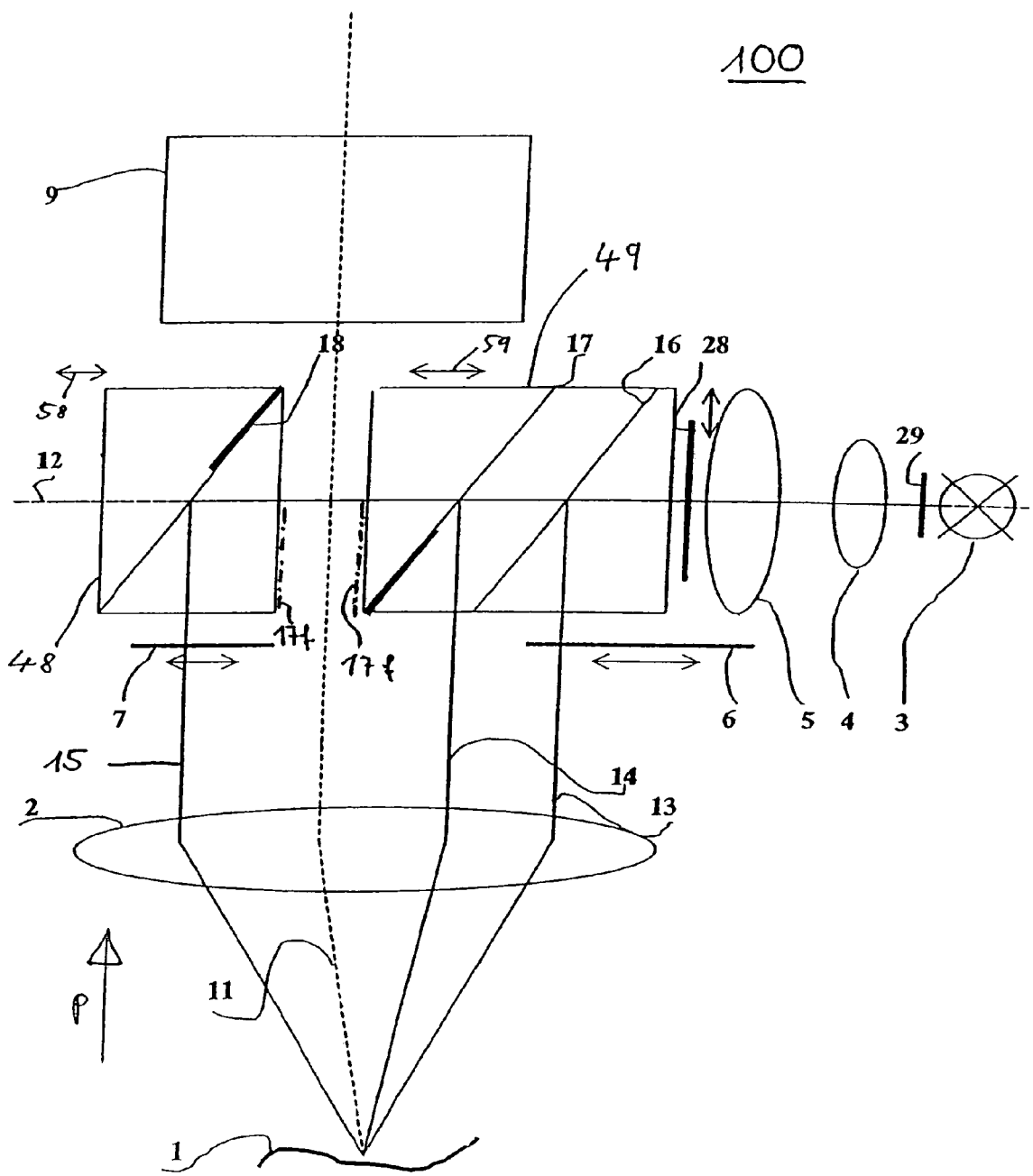
FIG. 4 shows the inventive microscope according to the invention according to FIG. 1 with another preferred embodiment of the lighting device according to the invention in a schematic lateral sectional view.

It is apparent from FIG. 4 that the microscope presented there basically corresponds to the microscope portrayed in FIG. 1, so that the shared components are identified by the same reference numerals. The microscope in FIG. 4 differs from the one in FIG. 1 in that the deflection element is not designed as a single unit prism block, but instead has two prism blocks 48, 49 which are physically separated from one another.

It is clear from FIG. 5 that, by removing two wedge-shaped sections 30a, 30b from a single unit prism block (as portrayed, for example, in FIG. 3), it is possible to provide a deflection device featuring two prism blocks as per the embodiment of FIGS. 4 and 5. The removal of these sections 30a, 30b proves to be advantageous in that it is effectively possible to eliminate areas covered by adhesive of the kind typically found on the boundary surfaces of deflection elements between the individual prisms of the prism blocks. This is favorable as, in practice, adhesive areas between two prisms cannot ideally be formed with parallel faces, and moreover the adhesive used features a different refraction index to the prisms to be attached together. On the whole this normally leads to reflection effects or refraction effects at the junction lines, potentially causing double images. These kinds of double images can largely be prevented both for the main surgeon and for the co-observer in accordance with the embodiment of the microscope according to the invention as presented in FIGS. 4 and 5. It should be noted that a prism combination featuring a two-prism block does not necessarily need to be provided by adapting or dividing a one-unit prism block, as illustrated here. It is also possible to create the two prism blocks separately from one another.

It is possible to insert glass blocks into the site of the removed sections 30a, 30b, which will ensure that the main surgeon and the co-observer experience the same observation conditions. It is also possible to omit these glass blocks entirely and to provide additional optically imaging lenses in the observation beam path of the co-observer or the main surgeon to balance any potential focal difference between the observation beam path of the main surgeon and the co-observer.

As already mentioned, +/−2° illumination enables optimal observation of the red reflex. Switching from +2° illumination to −2° illumination shall especially serve to improve the red reflex, for example, if the patient's eye is moved by the surgeon in the case of phacoemulsification. With conventional microscopes it was necessary to actively adjust a +/−2° mirror to the appropriate position by turning an adjusting knob. This invention enables straightforward, simultaneous +2° and −2° illumination, so that the surgeon's attention need not be diverted from the actual operation to making adjustments.

As a result of the easily variable overlapping of the fully mirror-coated areas on the deflection elements with the observation beam channels, optimal red reflexes can be obtained in both observation channels, for both the main surgeon and the assistant. +2° illumination is generally used for observing the red reflex in the case of a centred patient's eye. −2° illumination is particularly advantageous if the patient's eye is decentred.

The lighting device according to the invention is characterised by being extremely simple to operate during practical application. The fusion of the deflection elements into one single prism block or two prism blocks means that adjustments to create optimal distances between the deflection elements 16, 17, 18 can be either completely or largely avoided. In the embodiment shown in FIGS. 1 and 4 it is possible to move the prism block 8 or the two prism blocks 48, 49 relative to each other along the axis 12, as indicated clearly by means of double arrows 25, 58, 59.

It is also possible to provide the deflection elements 16, 17, 18 partly blackened. This measure enables the prevention of unwanted reflexes. It is also possible to fit absorbent elements, in particular plates, onto the underside and, with reference to FIG. 4, onto the inner side of the deflection device 8 or 48, 49, which also help to prevent unwanted reflexes due to multiple reflections. One such plate is shown schematically in FIG. 1 and is identified as 17e. Dotted lines are used in FIG. 4 to illustrate an absorbent surface covering which is designed as a light trap or optical filter, either blackened or selectively absorbent, which is designated 17f.

The blackening of the surfaces can also prevent internal reflexes in particular. The elements provided, for example the plate 17e or the surface covering 17f, can be used to prevent unwanted reflexes on the main objective.

The prism block according to FIG. 1 can be created by using two largely identical prism blocks which are rotated rotationally symmetrically to one another, wherein a parallelogram block is inserted between the rotationally symmetrically displaced prisms.

It should be noted that, in the embodiment of the microscope shown, the observation channels are largely arranged symmetrically around the observation axis 11. This observation axis does not necessarily correspond to the mid-axis or the optical axis of the main objective 2.

Finally, FIG. 6 illustrates a further embodiment of the deflection device according to the invention, viewed in a direction corresponding to the direction of the arrows P in FIG. 1 or FIG. 4. The deflection device formed as a prism block illustrated in FIG. 6 comprises two deflection elements 16, 17, where deflection element 16 is formed as a physical beam splitter and deflection element 17 is essentially fully mirror-coated. Corresponding to the illustrations in FIGS. 1–5, the lower edges 16a or 17a of the deflection elements 16 and 17 are shown. The respective upper edges have been omitted in these illustrations. For the sake of clarification it should be noted that the respective deflection elements or deflection surfaces 16a, 17a extend at an inclination to the right towards the plane of projection. Analogously to the embodiments of the lighting device according to the invention described hereinbefore, deflection element 16 serves to provide 6° illumination and deflection element 17 serves to provide +2° illumination. The observation beam paths 22a, 22b of the stereomicroscope are to the left of the deflection element 17, as illustrated in FIG. 6. According to this embodiment, glass blocks 60, 61 which are transparent for the observation beam paths 22a, 22b are inserted in these observation beam paths. Introducing glass blocks of this kind enables a contraction of the apertures (pupils) of the observation beam paths, which in turn allows for a reduction in the constructional height of the lighting device or the microscope. In addition, this kind of deflection device is shorter in the direction of the axis 12 shown than conventional deflection devices, in particular as the part of the deflection device directed towards the two observation beam paths 22a, 22b tapers in form in order to achieve optimal observation, free of vignetting. The glass blocks are expediently adhesively attached to the deflection device formed as a prism block. It is also possible to provide the glass blocks separately from the deflection device, so that they can be used only when required.

It should be noted that the light source is not shown in FIG. 6. In addition, only a lens, designated 4, is illustrated schematically, in connection with an optical system provided between the light source and the deflection device.

KEY TO REFERENCE NUMERALS

1 Object
2 Main objective
3 Light source
4, 5 Lenses
6, 7 Shutters
8 Deflection device (prism block)
8a Underside of the deflection device
8b Top side of the deflection device
9 Magnifying system
11 Optical axis 12 Axis of the deflection device
12a, b, c Partial beam
14, 15, 16 Partial beam
16, 17, 18 Deflection elements
16a, 17a, 18a Lower edges of the deflection elements
16b, 17b, 18b Upper edges of the deflection elements
17e Plate
17f Surface covering
19, 20 Mirror-coated areas of deflection elements 17, 18
22a, 22b Observation beam paths: main observer
23a, 23b Observation beam paths: co-observer
24 Mirror-coated area of deflection element 16
25 Double arrow
28, 29 Screens (shutters)
30a, 30b Wedge-like blocks
48, 49 Deflection device (prism blocks)
58, 59 Double arrows
60, 61 Glass blocks
100 Microscope

What is claimed is:

1. A lighting device for a surgical microscope for illuminating an observed object at various illumination angles relative to an observation beam path of the microscope, the lighting device comprising:
    an illumination system for emitting light; and
    a deflection device for deflecting the light emitted by the illumination system onto the object, wherein the deflection device includes three deflection elements, at least two of the deflection elements each being at least in part a physical beam splitter and two of the deflection elements are arranged to enable simultaneous +2° and −2° illumination of the object.

2. The lighting device according to claim 1, wherein the deflection device is a prism combination including partly reflective surfaces.

3. The lighting device according to claim 1, wherein the deflection device is a single-unit prism block.

4. The lighting device according to claim 1, wherein the deflection device includes at least two prism blocks spatially separated from one another.

5. A microscope for observing an object, the microscope comprising:
    a main objective;
    a magnifying system downstream of the main objective;
    four observation beam paths; and
    a lighting device including an illumination system for emitting light and a deflection device for deflecting the light emitted by the illumination system onto the object, the four observation beam paths passing through the deflection device, wherein the deflection device includes three deflection elements, two of the three deflection elements each being at least in part a physical beam splitter, and wherein at least one of the three deflection elements includes a surface that is, at least in part, fully reflective, and wherein two of the four observation beam paths are fully superimposed by a projection of the three deflection elements and another two of the four observation beam paths are partly superimposed by a projection of the three deflection elements;
    whereby the lighting device is operable to illuminate the object at a plurality of illumination angles relative to an observation beam path of the microscope.

6. The microscope according to claim 5, further comprising shutters for selectively switching illumination beam paths on or off.

7. The microscope according to claim 5, wherein the deflection device is transversely movable with respect to an optical axis of the microscope defined by the arrangement of the main objective and magnifying system relative to one another.

8. The microscope according to claim 5, further comprising glass blocks insertable into the observation beam paths.

9. A lighting device for a surgical microscope of a type having a pair of observation beam paths for a main observer and a pair of observation beam paths for a co-observer, the lighting device comprising:
    an illumination system for emitting light; and
    a deflection device arranged in the pair of observation beam paths of the main observer and in the pair of observation beam paths for the co-observer for deflecting the light emitted by the illumination system onto an object to be observed, wherein the deflection device includes a first deflection element, a second deflection element, and a third deflection element;
    the first deflection element being a beamsplitter reflecting a first partial beam for +6° illumination with respect to an observation beam path of an object to be observed and transmitting a second partial beam;
    the second deflection element including a fully reflective area in the shape of an arrow for reflecting a first portion of the second partial beam for +2° illumination with respect to an observation beam path of an object to be observed and transparent or semi-transparent areas bordering the fully reflective area, wherein the fully reflective area of the second deflection element overlaps only slightly with each of the pair of observation beam paths of the main observer and overlaps only slightly with one of the pair of observation beam paths of the co-observer; and
    the third deflection element including a fully reflective area in the shape of an arrow for reflecting a first portion of the second partial beam for −2° illumination with respect to an observation beam path of an object to be observed and transparent or semi-transparent areas bordering the fully reflective area, wherein the fully reflective area of the third deflection element overlaps only slightly with the other of the pair of observation beam paths of the co-observer.

* * * * *